(12) United States Patent
Kuehn

(10) Patent No.: US 12,011,575 B2
(45) Date of Patent: *Jun. 18, 2024

(54) ELECTRIC COUPLING FOR INJECTION DEVICES

(71) Applicant: Sanofi, Paris (FR)

(72) Inventor: Bernd Kuehn, Frankfurt am Main (DE)

(73) Assignee: Sanofi, Paris (FR)

( * ) Notice: Subject to any disclaimer, the term of this patent is extended or adjusted under 35 U.S.C. 154(b) by 246 days.

This patent is subject to a terminal disclaimer.

(21) Appl. No.: 17/592,945

(22) Filed: Feb. 4, 2022

(65) Prior Publication Data

US 2022/0152314 A1     May 19, 2022

Related U.S. Application Data

(63) Continuation of application No. 16/609,809, filed as application No. PCT/EP2018/060934 on Apr. 27, 2018, now Pat. No. 11,273,263.

(30) Foreign Application Priority Data

May 5, 2017   (EP) .................................. 17305518

(51) Int. Cl.
    *A61M 5/315*     (2006.01)

(52) U.S. Cl.
    CPC .... *A61M 5/31568* (2013.01); *A61M 5/31511* (2013.01); *A61M 2205/3368* (2013.01); *A61M 2205/3553* (2013.01); *A61M 2205/3584* (2013.01); *A61M 2205/50* (2013.01); *A61M 2205/502* (2013.01); *A61M 2205/8212* (2013.01)

(58) Field of Classification Search
    CPC .......... A61M 5/31568; A61M 5/31511; A61M 2205/50; A61M 2205/502
    See application file for complete search history.

(56) References Cited

U.S. PATENT DOCUMENTS

| 5,304,128 A | 4/1994 | Haber et al. |
| 2004/0049151 A1 | 3/2004 | Lell |
| 2011/0172634 A1 | 7/2011 | Gonnelli et al. |
| 2011/0313349 A1 | 12/2011 | Krulevitch et al. |
| 2015/0190590 A1 | 7/2015 | Richter et al. |

(Continued)

FOREIGN PATENT DOCUMENTS

| CN | 102413855 A | 4/2012 |
| CN | 104519930 A | 4/2015 |

(Continued)

OTHER PUBLICATIONS

International Preliminary Report on Patentability in Application No. PCT/EP2018/060934, dated Nov. 5, 2019, 7 pages.

(Continued)

*Primary Examiner* — Bradley J Osinski
(74) *Attorney, Agent, or Firm* — Fish & Richardson P.C.

(57) ABSTRACT

Embodiments of the present disclosure are directed to conserving energy of an injection device that includes an energy source, an electronic component configured to be electrically decoupled from the energy source, a priming component configured to generate a trigger, and a mechanism attached to the priming component and configured to perform operations comprising in response to receiving the trigger, electrically coupling the energy source to the electronic component.

26 Claims, 9 Drawing Sheets

(56) References Cited

U.S. PATENT DOCUMENTS

2015/0202376 A1     7/2015   Haupt
2015/0359967 A1   12/2015   Steel et al.
2017/0000955 A1     1/2017   McLoughlin et al.

FOREIGN PATENT DOCUMENTS

| CN | 104703642 A | 6/2015 |
|---|---|---|
| CN | 104955503 A | 9/2015 |
| JP | 2004-500933 | 1/2004 |
| JP | 2004-520884 A | 7/2004 |
| JP | 2012-245411 | 12/2012 |
| JP | 2015-505682 | 2/2015 |
| JP | 2016-510241 | 4/2016 |
| KR | 10-1587235 | 1/2016 |
| WO | WO 2002/051470 | 7/2002 |
| WO | WO 2013/072444 | 5/2013 |
| WO | WO 2014/128155 A1 | 8/2014 |
| WO | WO 2014/190223 | 11/2014 |

OTHER PUBLICATIONS

International Search Report and Written Opinion in Application No. PCT/EP2018/060934, dated Jul. 18, 2018, 10 pages.

ELECTRIC COUPLING FOR INJECTION DEVICES

CROSS-REFERENCE TO RELATED APPLICATIONS

The present application is a continuation application of U.S. patent application Ser. No. 16/609,809, filed on Oct. 31, 2019, which is the national stage entry of International Patent Application No. PCT/EP2018/060934, filed on Apr. 27, 2018, and claims priority to Application No. EP 17305518.7, filed on May 5, 2017, the disclosures of which are incorporated herein by reference.

TECHNICAL FIELD

This disclosure relates to an injection device, and more particularly, to a cartridge of an injection device for sensing a dosage of a medicament to be administered.

BACKGROUND

The life of an electronically-enabled injection device can be dictated by the life of its energy supply. Some electronically-enabled injection devices can be kept on shelves for years before being used. Current configurations of electronically-enabled injection devices lead to idle drainage of the energy supply, such that, even if the electronically-enabled injection device has not been used, long shelf life can exhaust the life of the energy supply. A low battery condition can lead to no- or malfunction of the device, an incorrect dosage, it can lead to a missed dosage, or it can even make the electronically-enabled injection device unusable by stopping the operation of the electronic components.

SUMMARY

Embodiments of the present disclosure include coupling mechanisms and systems configured for extending the life of electronically-enabled injection devices by preventing idle drainage of the energy source. In accordance with one aspect of the present disclosure, an electronically-enabled injection device includes an energy source, an electronic component configured to be electrically decoupled from the energy source, a priming component configured to generate a trigger, and a mechanism attached to the priming component and configured to perform operations including in response to receiving the trigger, electrically coupling the energy source to the electronic component.

In some embodiments, the mechanism includes a switch configured to be activated for electrically coupling the energy source to the electronic component. In some embodiments, the energy source is moveable between two positions. In some embodiments, the mechanism is configured to couple the energy source to the electronic component by moving the energy source from a first position, in which the energy source is electrically decoupled from the electronic component to a second position, in which the energy source is electrically coupled with the electronic component. In some embodiments, the electronic component includes two contact plates. In some embodiments, the energy source includes two pins configured to couple with the two contact plates. In some embodiments, the electronic component is included in a plunger stopper. In some embodiments, the energy source is attached to at least one of a bearing, a plunger rod, and a cavity in a plunger head. In some embodiments, the pins are configured to pierce at least a portion of the plunger stopper for electrically coupling with the electronic component. In some embodiments, the energy source is attached to a plunger rod separated from the bearing by an electrically insulating membrane and configured to move in a distal direction during priming and dispensing. In some embodiments, the pins are configured to pierce the electrically insulating membrane for electrically coupling with the electronic component. In some embodiments, the priming component is configured to enable a user to dial a dose of a medicament to be expelled by the injection device. In some embodiments, the electronic component is decoupled from the energy source after dispensing the medicament.

In accordance with another aspect of the present disclosure, a medicament injection system includes: an injection device including: an energy source, an electronic component configured to be electrically decoupled from the energy source, a priming component configured to generate a trigger, and a mechanism attached to the priming component and configured to performing operations including in response to receiving the trigger, electrically coupling the energy source to the electronic component, and an external processor configured to communicate with the electronic component.

In some embodiments, the electronic component includes an antenna configured to transmit the electric signal to the external processor. In some embodiments, the external processor is configured to perform operations including: receiving a user input indicating that a medicament is to be expelled by the injection device, and transmitting to the priming component of the injection device a signal to generate the trigger. In some embodiments, the antenna is configured to transmit the amount of the medicament to be expelled. In some embodiments, the medicament injection system can include a support configured to attach the energy source to a component of the injection device. In some embodiments, the support includes a shape configured to transmit a dispensing force from the priming component to electrically couple the energy source to the electronic component. In some embodiments, the support includes at least one of a cage and a crown shape.

In accordance with yet another aspect of the present disclosure, a method for electrically activating an injection device includes: generating a trigger, in response to generating the trigger, electrically coupling an energy source with an electronic component of the injection device, and in response to electrically coupling, generating, by the electronic component, an electric signal associated to a medicament to be expelled by the injection device.

It is appreciated that systems in accordance with the present disclosure can include any combination of the aspects and features described herein. That is to say that methods in accordance with the present disclosure are not limited to the combinations of aspects and features specifically described herein, but also include any combination of the aspects and features provided.

Electronically-enabled injection devices allow patients to safely administer a medicament, without the need for constant supervision by medical staff, while enabling transmission of treatment data to the medical staff. Electronically-enabled injection devices can include a medicament reservoir like a cartridge or syringe, a mechanical component, an electronic component, and an energy supply. The energy supply can be a battery, which supplies power to the electric component.

The details of one or more embodiments of the present disclosure are set forth in the accompanying drawings and

BRIEF DESCRIPTION OF THE FIGURES

Like reference symbols in the various drawings indicate like elements.

DETAILED DESCRIPTION

Figure 1A:
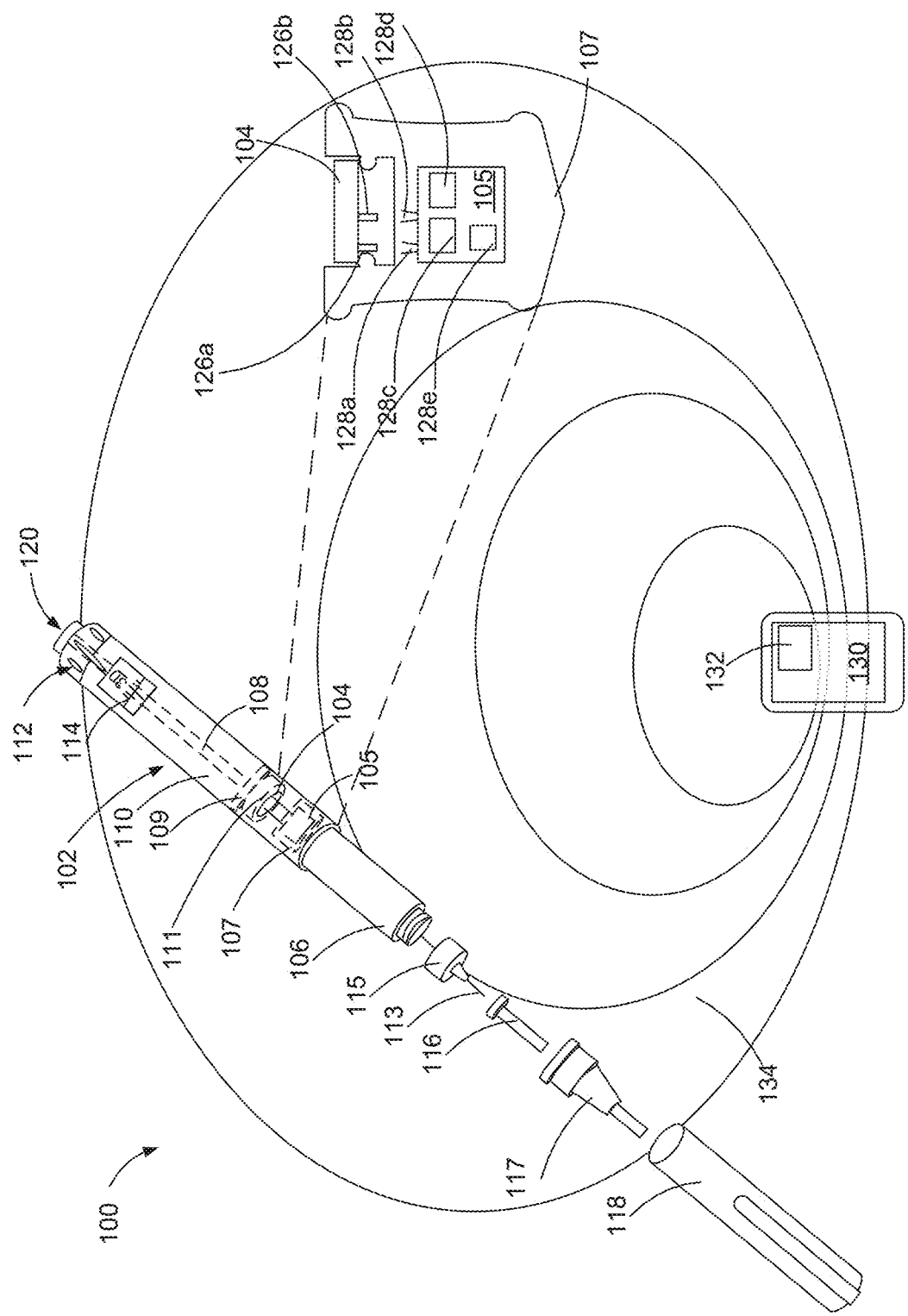
FIGS. 1A-1E are exploded views of examples of devices.

Embodiments of the present disclosure are generally directed to controlled coupling of an energy source to an electronic component of an injection device to prevent idle drainage of the energy source. More particularly, embodiments of the present disclosure are directed to a mechanism configured to receive a trigger signal and in response to receiving the trigger signal, electrically coupling the energy source of the injection device to the electronic component.

The subject matter described will largely be described with reference to a drug delivery device such as an injection device (e.g., an insulin injection device). However, the systems and techniques described are not limited to such applications, and may equally well be deployed with injection devices that eject other medicaments, or with other types of medical devices (e.g., pumps).

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

In some injection devices, electric coupling of the energy source with the electronic component prior to usage of the injection device can lead to idle drainage of the energy source. Accordingly, use of electronic injection devices can be hindered by such idle drainage of the energy source. As described in further detail herein, embodiments of the present disclosure address this challenge. For example, in accordance with embodiments, the electronic components of the electronic injection device can be configured to be decoupled from an energy source until a trigger signal is initiated (e.g., during a priming step of a medicament administration) to prevent idle drainage of the energy source.

FIGS. 1A-1F illustrate exploded views of example fluid delivery systems 100. The example fluid delivery systems 100 can be configured to assist a user in injecting a fluid (e.g., a medicament) and facilitate sharing of medical data. The example fluid delivery systems 100 can include an injection device 102 and an external device 130. The injection device 102 can be configured to prevent idle drainage of an energy source 104. The injection device 102 can be a pre-filled, disposable injection pen or the injection device 102 can be a reusable injection pen.

The injection device 102 can be configured to communicate with the external device 130. The injection device 102 can transmit to the external device 130 operational data (e.g., data and time of start of usage of injection device 102, temperature of injection device 102 during use and storage) and corresponding treatment data (e.g., amount and time of medicament dispensed by the injection device 102). In some embodiments, the injection device 102 can be associated with an identifier that is used by the external device 130 to uniquely identify the injection device 102.

The injection device 102 can include a housing 110 and a needle assembly 115. The housing 110 can contain the energy source 104, an electronic system including at least one electronic component 105, a medicament reservoir 106, a stopper 107, a plunger rod 108, a plunger head 109, a bearing 111, a dosage knob 112, a dosage window 114, and an injection button 120. The housing 110 can be molded from a medical grade plastic material such as a liquid crystal polymer. The energy source 104 can be a disposable or rechargeable battery, such as a 1.5V-5 V silver-oxide or lithium battery (e.g., SR626, SR516, SR416) or a super capacitor. In some embodiments, energy source 104 can include a plurality of batteries (e.g., two 1.5V batteries). The energy source 104 can be configured to supply energy to the electronic component 105 under particular conditions, such as after a priming step is performed. For example, the energy source 104 can include a pair of pins 126a, 126b. The pins 126a, 126b can be configured to electrically couple with the contact plates 128a, 128b of the electronic component 105.

The electronic system can include one or more electronic components 105 configured to perform and/or assist with one or more functions of the injection device 102 (e.g., the ejection of the medicament) upon coupling with the energy source 104. For example, the electronic component 105 can include at least one of the pair of contact plates 128a, 128b, an antenna 128c, a sensor 128d (e.g., a feedback sensor, a temperature sensor), one or more processors 128e, and a motor. The motor can be configured to advance in micro-step increments to dispense a particular amount of medicament. The feedback sensor can provide, to the one or more processors, a signal (e.g., a voltage), which is proportional to the amount of medicament dispensed. The one or more processors 128e can include a microprocessor. In some embodiments, the microprocessor is a microcontroller, e.g., a combination of microprocessor components and other components formed in a single package. The microprocessor can be an arithmetic and/or a logic unit array. The one or more processors 128e can process one or more signals received from other electronic components 105 of the electronic system and transmit a signal to the antenna 128c. For example, the one or more processors 128e can be configured to execute operations on received data to generate output data, as described in detail with reference to FIG. 3. The one or more processors 128e can be configured to determine the amount of the fluid within the injection device 102 based at least in part on an electrical signal and transmit the data including the amount of the fluid to the antenna 128c that can transmit it to the external device 130.

The antenna 128c can be a bluetooth or near-field communication (NFC) antenna. The antenna 128c can be configured to transmit signals to the one or more processors 128e and to the external device 130. The signals transmitted by the antenna 128c can include the amount of the fluid in the medicament reservoir 106, values measured by the sensor 128d, and the identifier of the injection device 102. The communication field 134 can be a bluetooth field or an NFC field, generated by the external device 130. The external device 130 can include a bluetooth or a RF module, a transmitter, a receiver, and an external processor 132. The external processor 132 can be configured to process the data transmitted by the injection device 102. The external device 130 can be configured to display (e.g., through a graphical user interface) the data received from the injection device 102 and processed by the external processor 132.

The medicament reservoir 106 can be configured to contain a fluid medicament. The medicament reservoir 106 can be a conventional, generally cylindrical, disposable container like a cartridge or a syringe used to package prepared fluids such as medicaments, anesthetics and the like. The medicament reservoir 106 can be provided with a pair of ends, one end having a pierceable membrane, which receives an inward end of needle 113 in sealing engagement. A dose of the contained medicament can be ejected from the injection device 102 by turning the dosage knob 112, and the selected dose is then displayed via dosage window 114, for instance in multiples of so-called International Units (IU), wherein one IU is the biological equivalent of about 45.5 micrograms of pure crystalline medicament (1/22 mg). An example of a selected dose displayed in dosage window 114 may for instance be 30 IUs, as shown in FIG. 1A. In some embodiments, the selected dose can be displayed differently, for instance by an electronic display (e.g., the dosage window 114 may take the form of an electronic display). Turning the dosage knob 112 can cause a mechanical click sound to provide acoustical feedback to a user.

The numbers displayed in dosage window 114 can be printed on a sleeve that is contained in housing 110 and mechanically interacts with a plunger head 109 that is fixed at the end of the plunger rod 108 and pushes the stopper 107 of the medicament reservoir 106. The bearing 111 can provide firm mounting to one or both ends of the plunger rod 108.

The plunger head 109 (e.g., a back end of the plunger) can be configured to expel a portion of the fluid by displacing the stopper 107 contained within the medicament reservoir 106, such that a position of the stopper 107 is associated with an amount of the fluid within the injection device 102. The stopper 107 can be a flexible stopper, such as a rubber stopper, configured to be pierceable by the pair of pins 126a, 126b. The stopper 107 can have an outwardly projecting rim matching the geometry and dimensions of the energy source 104. The stopper 107 can be of a sufficient length so that the stopper 107 is not ripped or twisted when being engaged by the plunger head 109.

The needle assembly 115 includes a needle 113 that can be affixed to the housing 110. The needle 113 can be covered by an inner needle cap 116 and an outer needle cap 117, which in turn can be covered by a cap 118. When needle 113 is stuck into a skin portion of a patient, and then injection button 120 is pushed, the medicament dose displayed in dosage window 114 can be ejected from injection device 102. When the needle 113 of injection device 102 remains for a certain time in the skin portion after the injection button 120 is pushed, a high percentage of the dose is actually injected into the patient's body. Ejection of the medicament dose can generate a mechanical click sound, which can be different from the sounds produced when using dosage knob 112.

Injection device 102 can be used for several injection processes until either medicament reservoir 106 is empty or the expiration date of injection device 102 (e.g., 28 days after the first use) is reached. Before using injection device 102 for the first time, it may be necessary to perform a priming operation to couple the energy source 104 to the electric component and/or to remove air from medicament reservoir 106 and needle 113. For instance, the priming operation can include selecting two units of medicament and pressing injection button 120 while holding injection device 102 with the needle 113 upwards. The impulse generated by selecting two units of medicament or pressing injection button 120 can trigger the electrical coupling of the energy source 104 with the electronic component 105. For example, as illustrated in FIGS. 1A-1D, the impulse generated by selecting two units of medicament or pressing injection button 120 can be transmitted by the plunger rod 108, leading to a shift of the energy source 104 from a first position, in which the pins 126a, 126b of the energy source 104 are uncoupled from the contact plates 128a, 128b of the electronic component 105, to a second position, in which the pins 126a, 126b of the energy source 104 are electrically coupled to the contact plates 128a, 128b of the electronic component 105.

Figure 1B:
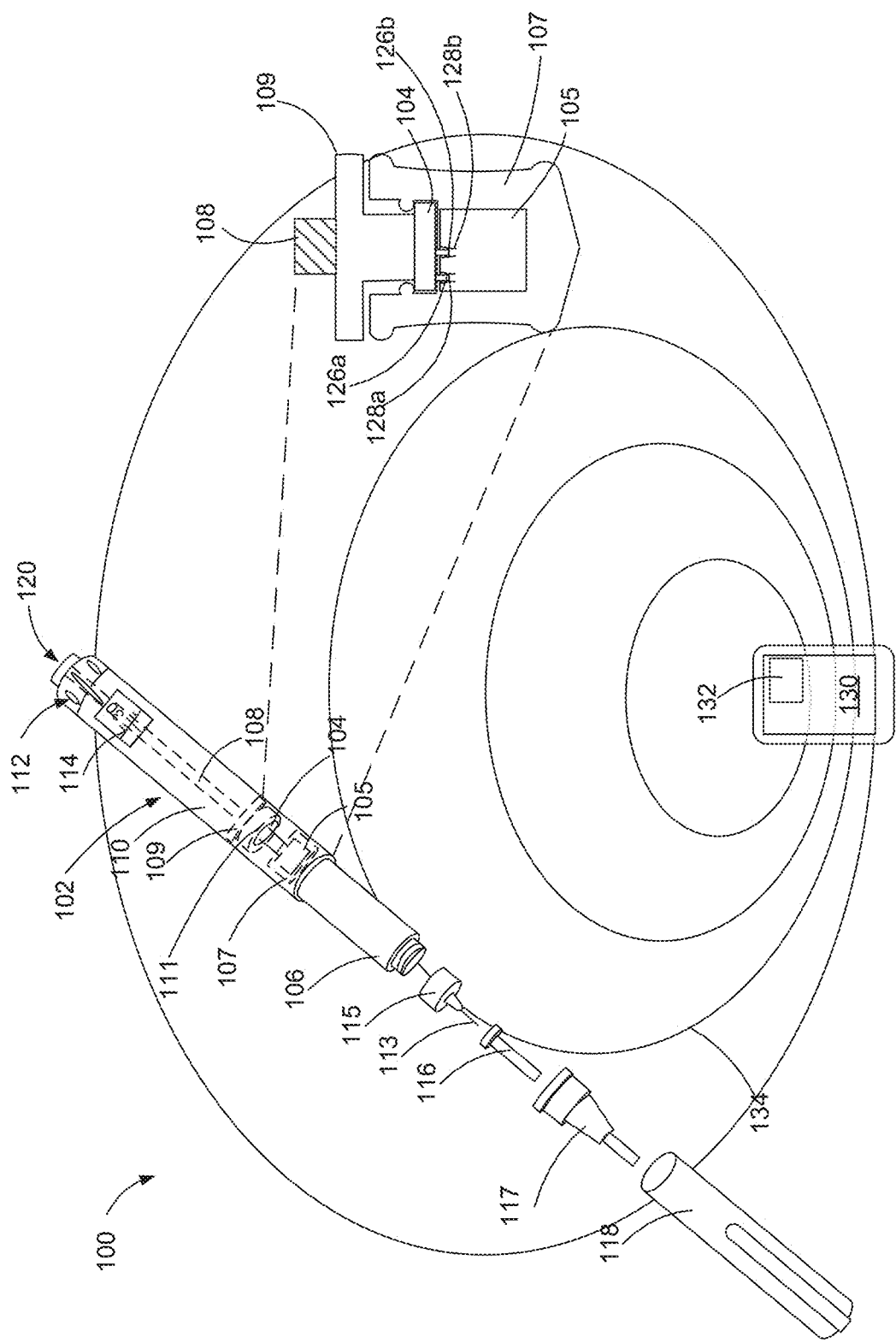
Figure 1C:
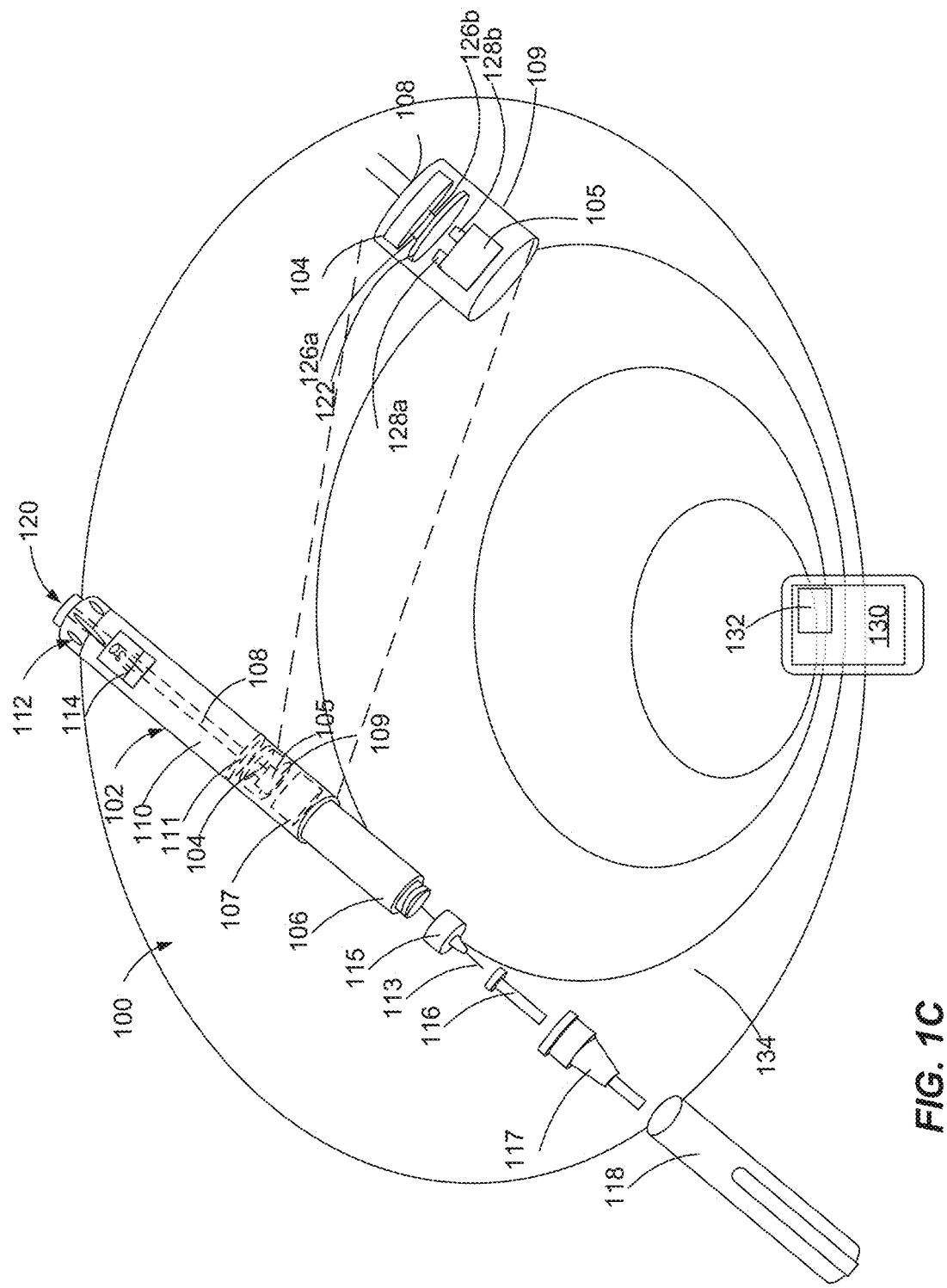
Figure 1D:
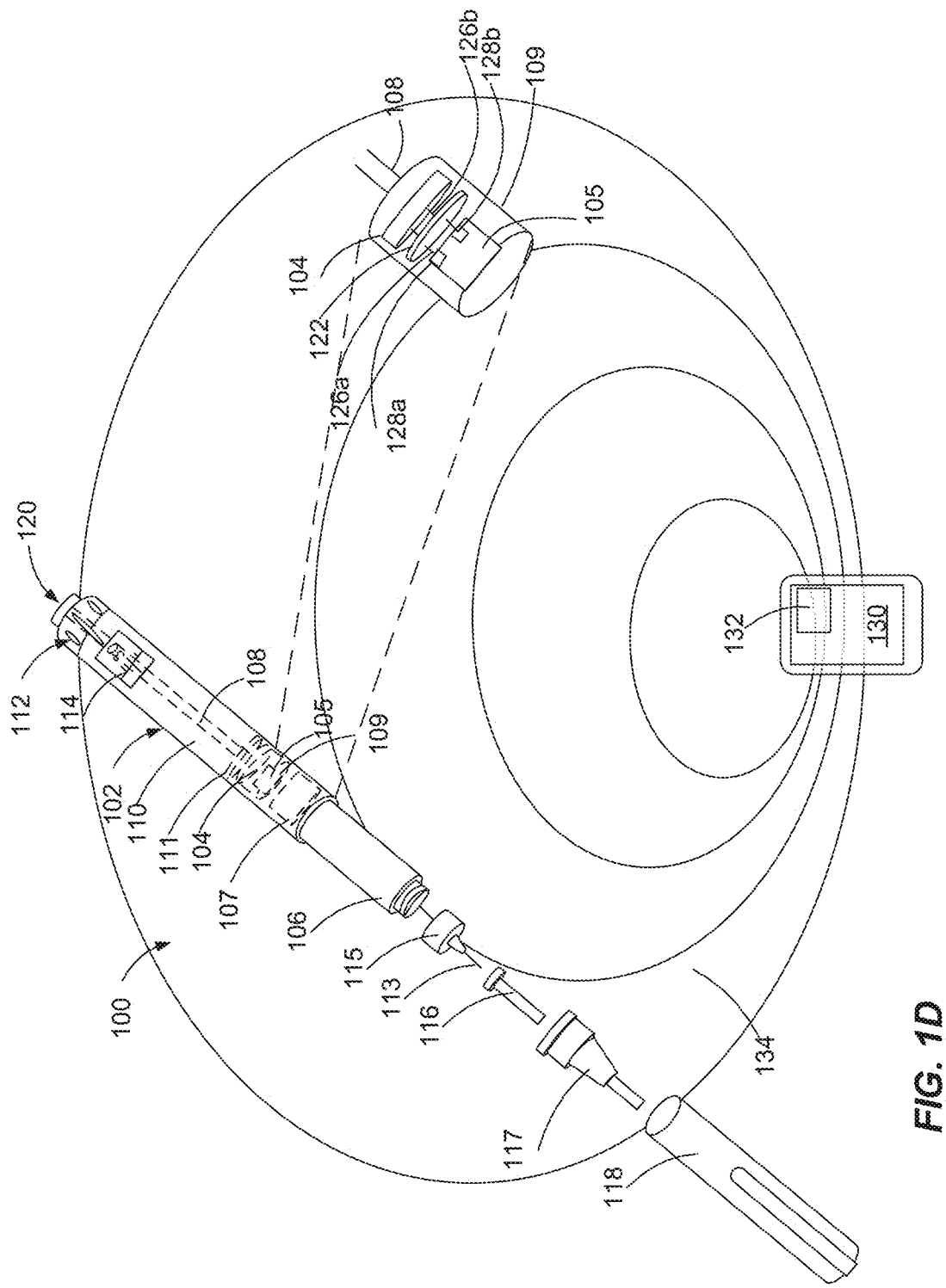

In some embodiments, the electronic components 105 of the electronic system can be integrated within the housing 110 at a single location, or at multiple locations (e.g., within or attached to a plunger rod 108, and a cavity in the plunger head 109). The location of one or more electronic components 105 of the electronic system, such as the pair of contact plates 128a, 128b and/or the location of the energy source 104 can be selected to maintain the electronic component 105 and hence the entire electronic system decoupled from the energy source 104 prior to the usage of the injection device 102 (e.g., prior to a priming operation). In some embodiments, as illustrated in FIGS. 1A, 1B, 1E, and 1F, one or more components 105 of the electronic system including the contact plates 128a, 128b can be contained within the stopper 107, such that the contact plates are surrounded by electrically insulating material (e.g., the ends of the contact plates 128a, 128b are at least 0.1 mm away from the nearest external surface of the stopper 107). In some embodiments, as illustrated in FIGS. 1C and 1D, one or more electronic components 105 of the electronic system including the contact plates 128a, 128b can be contained within the plunger head 109, being separated by an electrically insulating membrane 122 from the pins 126a, 12b.

Figure 1E:
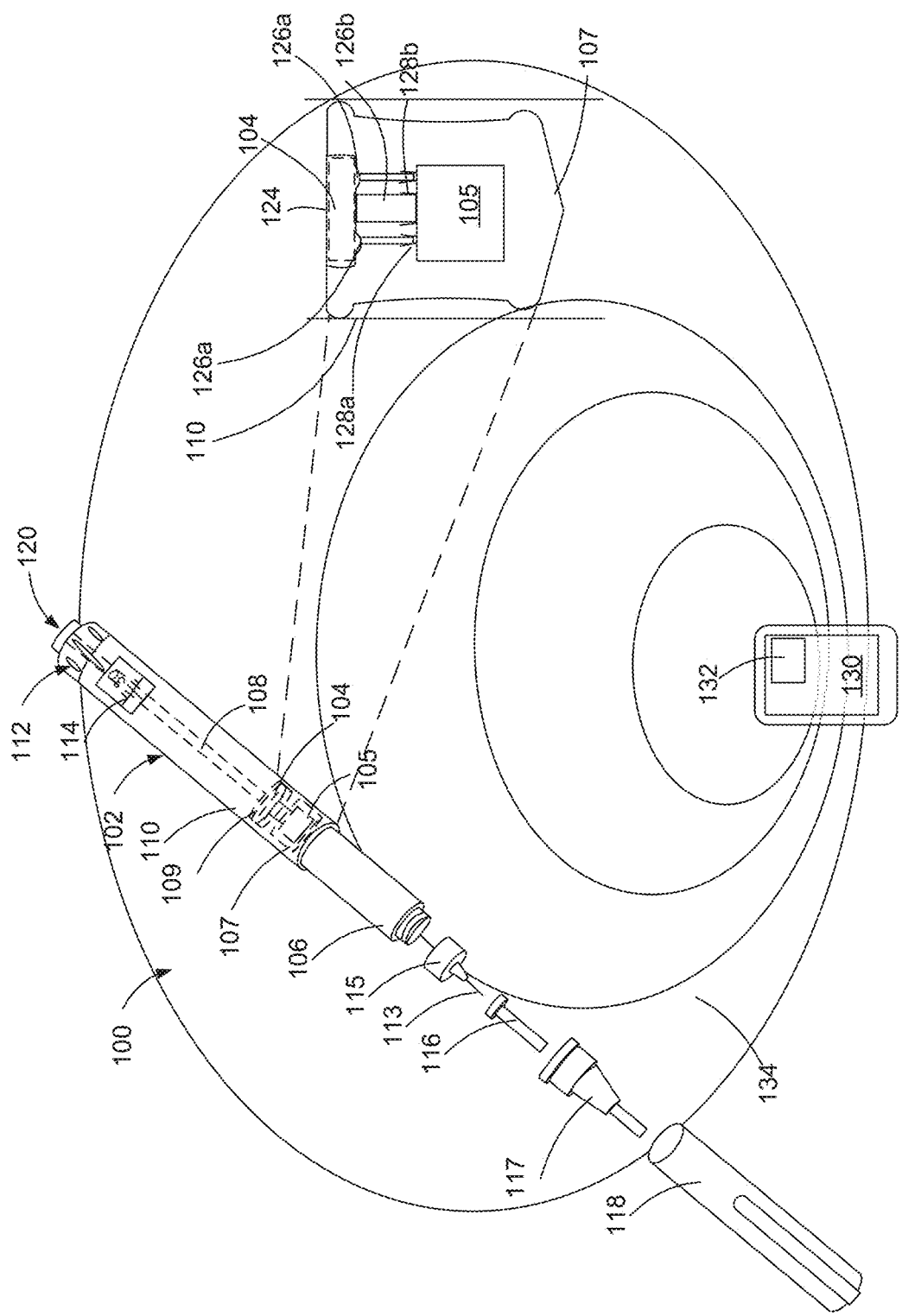

In some embodiments, the location of the energy source 104 and/or the location of one or more electronic components 105 of the electronic system can be selected independent from the coupling between the electronic component 105 and the energy source 104. In some embodiments, one or more characteristics of one or more electronic components 105 of the electronic 105 and/or one or more characteristics of the energy source 104 can be selected to couple and/or uncouple the electronic component 105 from the energy source 104. As illustrated in FIGS. 1A, 1C, and 1E, the configuration of the contact plates 128a, 128b can be set to extend outwardly from the perimeter of the electronic component 105. As illustrated in FIGS. 1B and 1D, the configuration of the contact plates 128a, 128b can be set to extend inwardly from the perimeter of the electronic component 105.

In some embodiments, the housing 110 of the injection device 102 can be configured to be separated in multiple segments to enable a user to attach the energy source 104 to a component of the injection device 102 (e.g., plunger stopper 107, plunger rod 108 or plunger head 109) and/or attach at least a component of the electronic component 105 to a component of the injection device 102 (e.g., stopper 107 or plunger head 109). The examples illustrated in FIGS. 1A, 1B, and 1E-1H include an energy source 104 attached to the plunger head 109. The examples illustrated in FIGS. 1C and 1D include an energy source 104 included in the plunger head 109. Even though not illustrated, the energy source 104 can be attached to or placed in the plunger rod 108 and can be customized to fit into the geometry of the plunger rod 108. Within the example of the energy source 104 attached to the plunger rod 108, the connections to the electronic component 105 are configured to cross the plunger head 109.

In some embodiments, and as illustrated in FIGS. 1E-1H, the injection device 102 includes an additional component configured to attach the energy source 104 to a component of the injection device 102 (e.g., back-end of the plunger stopper). The additional component can include a support 124 and/or a battery contact (cathode 126a and anode 126b). The support 124 and/or the battery contact 126a can include a shape that enables good transmission of the applied dispensing force from the priming component (e.g., dosage knob 112 via the plunger rod 108, and the plunger head 109) onto the stopper 107. For example, the support 124 and/or the battery contact 126a can be shaped like a "crown" or "cage." The support 124 and/or the battery contact 126a can be configured to hold the battery cell in a particular position and can enable precise positioning of the electronic component 105 during molding steps of the plunger head 109 and/or plunger stopper 107.

Figure 1F:
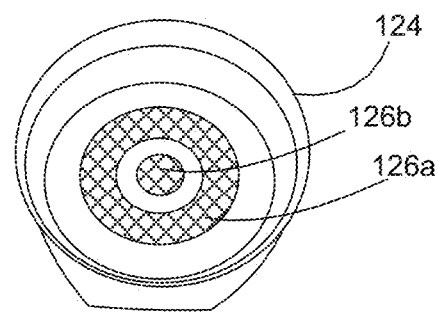
FIGS. 1F-1H are examples of components of devices.
Figure 1G:
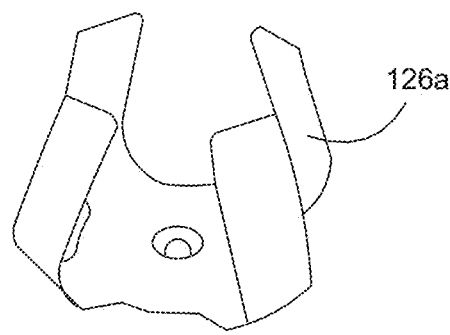
Figure 1H:
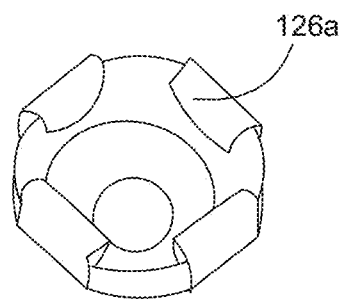

Examples of a support 124, cathode contacts 126a (−) and anode contacts 126b (+) are shown in FIGS. 1F, 1G and 1H. For example, FIG. 1F illustrates a cage shaped battery cell cavity where the cathode 126a (−) is ring shaped and the anode 126b (+) is a centred pin. The energy source 104 can be held in place by the support 124, which includes a snap fit of surrounding flexible (e.g., rubber) material. FIG. 1G illustrates a crown shaped cathode 126a (−) with flexible arms to center the energy source 104 and configured to provide good lateral contact with the housing of the energy source 104. FIG. 1H illustrates a cage shaped cathode 126a (−) configured to center the energy source 104 and to provide good lateral contact with the housing of the energy source 104. Even though FIGS. 1G and 1H illustrate the battery contact as including four arms, the battery contact can include any plurality of arms, which can be symmetrically distributed around the circumference of the support 124.

In some embodiments, the housing 110 of the injection device 102 can be configured to be separated or broken in multiple segments to provide a user access to the energy source 104, to enable separate disposal of the energy source 104. In some embodiments, the medicament reservoir 106 to be assembled with the injection device 102 is manufactured with inserted stopper 107, is filled with the fluid medicament and is closed with a crimp seal. During the manufacturing and storage of the medicament reservoir 106 prior to assembly with the injection device 102, the energy source 104 is not attached to the medicament reservoir 106. By keeping the energy source 104 detached from the electronic components, no idle drainage of energy can occur during manufacturing and potential long storage of the medicament reservoir 106. In the subsequent step of device assembly, the energy source 104 is attached to the injection device 102 by keeping the energy source 104 disconnected from the electronic component 105. In some embodiments, the energy source 104 can be connected at this step of device assembly to the electronic component 105 to enable controls of functionality of the injection device 102. Connection to the energy source 104 as manufacturing step allows to wake-up the electronic component 105 and to generate feedback signals that confirm proper system functionality. After performing such in-process controls, the energy source 104 may be disconnected again, or the electronic component 105 or the entire electronic system may be set in sleep-mode through appropriate software features that reduce energy consumption until the priming step is performed to wake-up the electronic component 105 and/or the electronic system.

Figure 2:
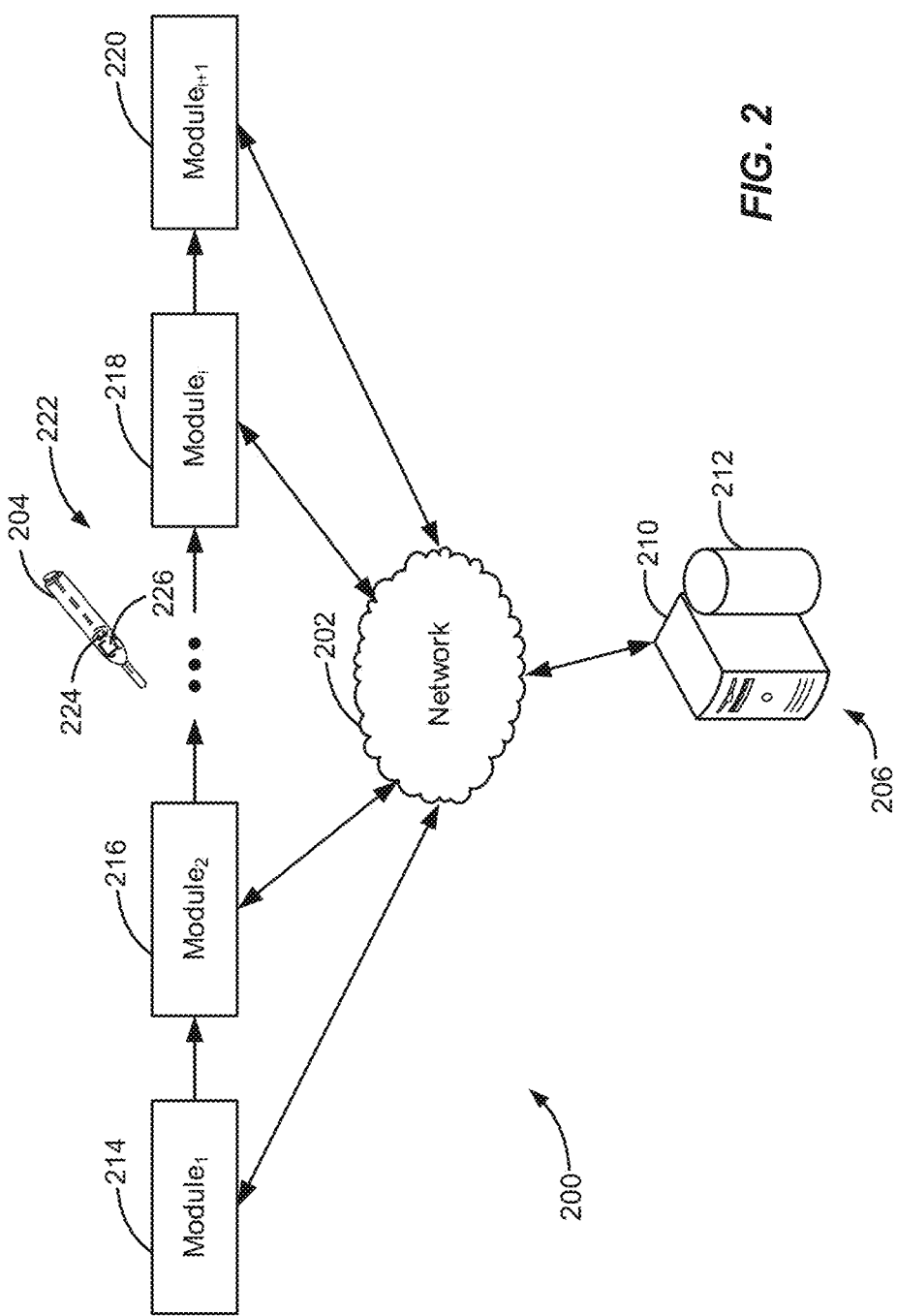
FIG. 2 is a block diagram of an example system.

FIG. 2 is a block diagram of an example system 200 that can execute embodiments of the present disclosure. The system 200 enables n number of entities (examples of which are entities 214, 216, 218, 220) transfer and access, by way of a network 202, to a central computer 206 that includes a central database 212 and a central server 210.

In the example of FIG. 2, an entity (e.g., entities 214, 216, 218, 220) can be a medicament supplier, a medical facility (e.g., a healthcare provider) or a patient located in a healthcare continuum 222. For example, entity 214 is located before entity 216 in the healthcare continuum 222. Entity 218 is located before entity 220 in the healthcare continuum 222. The healthcare continuum 222 can manufacture, store, transport, and use the injection device 204. The injection device 204 along with any additional components (e.g., energy source 224 and electrical component 226) can be transferred between multiple entities in the healthcare continuum 222 (e.g., from medicament supplier, to healthcare provider working within a medical facility, and to patient) during the medical care process.

The injection device 204 (e.g., fluid delivery system 100 described with reference to FIGS. 1A and 1B) can include an energy source 224 uncoupled from the electrical component 226 (e.g., energy source 104 described with reference to FIGS. 1A and 1B) in an initial state (e.g., prior to a priming step). Each entity along the healthcare continuum 222 can hold and transfer the injection device 204 without idly depleting the energy source 224. One of the entities within the healthcare continuum 222 can perform a priming step on the injection device 204, in response to which the energy source 224 is coupled to the electronic component 226. In response to coupling the energy source 224 to the electronic component 226, the electronic component 226 can generate an item-level data. The item-level data can be associated with the unique identification number of the injection device 204 for storage in the central database 212. The item-level data can be transmitted to another device (e.g., the central database 212 of the central computer 206) by using bluetooth or NFC communication.

In some embodiments, the central computer 206 is located at an external service provider. Shared data among entities in the healthcare continuum 222 can be stored in the central database 212. Each entity in the healthcare continuum (the n entities in the healthcare continuum 222) can outsource the shared data to the external service provider. In addition, the external service provider can manage access to the stored shared data. For example, the central database 212 may be a cloud storage and the central computer 206 may be a cloud computing system hosted by a third party or service provider. The cloud storage service provider can manage and maintain the central database 212 where the entities 214, 216, 218, 220 can store item-level data for sharing and exchanging among the entities 214, 216, 218, 220.

Each entity (e.g., entities 214, 216, 218, 220) can encrypt and store item-level data for an injection device 204 used within the healthcare continuum 222 (e.g., in association with injection of a medicament) in the central database 212. Security requirements for the central database 212 can prevent a party observing the central database 212 from accessing data received from the injection device 204 without authorization. The entity that owns the data (e.g., the user of the injection device 204) included in the central database 212 can enforce various levels of access control to the item-level data for its injection devices. For example, regarding injection device 204, the data owner (e.g., patient) can provide access control to item-level data for injection device 204 to another entity (e.g., healthcare provider) based on the association with the other entity (e.g., through the corresponding medical facility).

In some embodiments, a patient can provide individual access to a physician for each item-level data stored for the injection device 204 in the central database 212. The data access control allows the patient to set the access level to each individual tuple of the item-level data. In some embodiments, a healthcare administrator can provide a healthcare provider access to all tuples of item-level data for an item that a medical facility possessed at one time. For example, a healthcare administrator can use the access control for item-level tracking. The healthcare administrator can allow or restrict the visibility of items on an item-by-item basis to other entities that at one time may have had possession of the item or may have been associated with the item (e.g., only healthcare providers associated with a particular type of medical treatment delivered to corresponding patients would be granted access to the data). This can allow one entity (e.g., the healthcare administrator) to provide item-level data access to other entities without having to set individually the access control of each tuple of the item-level data to each individual entity. For example, entities, including the healthcare administrator, may then engage in fair data sharing agreements for an item with one another without the risk of disclosing sensitive or confidential information, either directly or by inference, regarding each individual item or entity.

In some embodiments, a healthcare administrator or a patient can provide an entity access to all item-level data. For example, the entity can be a trusted third party (e.g., a patient, a healthcare provider, a medicament supplier or other third parties) full access to all tuples of the item-level data. In the case where the central database 212 may be cloud storage and the central computer 206 may be a cloud computing system hosted by a third party or service provider, the access level may be used between the healthcare administrator or the patient and the service provider in order for the service provider to manage and maintain the central database 212 and provide automatic refills based on the data generated after coupling the energy source 224 to the electronic component 226.

The tracking of use of an injection device 204 by a medical entity may allow the medical entity to identify deviations from treatment, enabling the medical entity to provide guidance to the user of the injection device in following the treatment. For example, the item-level data can include a unique identifier for the injection device 204, an amount of fluid within a cartridge and/or injection device, a timestamp of coupling the energy source 224 to the electronic component 226, a location, and a situation specific data for the injection device. The medical entity can record or store the elements in a "tuple" as item-level data in a data repository for the healthcare provider. In some embodiments, the data repository can be located within a medical facility. In some embodiments, the data repository can be located outside of the medical facility. For example, the data can be stored in a data repository provided by a cloud service provider. Entities in the healthcare continuum sharing data may need to gain access to data provided by multiple healthcare providers.

Accordingly, and in some embodiments, healthcare providers in a healthcare continuum can share a common database for use as a central repository for item-level data. A service provider or third party may manage the resources of the shared central repository. Sharing and exchanging of data generated by the injection device after coupling the energy source 224 to the electronic component 226, among medical facilities in the healthcare continuum, can enable the use of various applications for analysis of the data. For example, anti-counterfeiting applications, healthcare continuum bench marking applications and applications that identify compliance with healthcare rules and regulations can use the data of the injection device to provide information to the healthcare providers and/or entities in the healthcare continuum.

Figure 3:
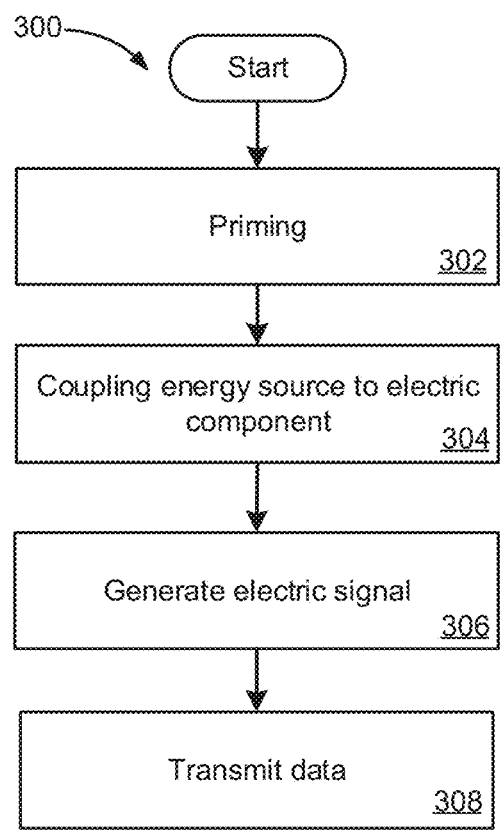
FIG. 3 is a flowchart illustrating an example.

FIG. 3 is a flowchart illustrating an example process 300 that can be executed by devices and systems described with reference to FIGS. 1 and 2. The process 300 begins by performing a priming operation on an injection device having an energy source uncoupled from an electronic component (302). The priming operation can be initiated by a user of the injection device. An example of a priming operation performed with the injection device can include selecting a particular number (e.g., one or two) units of medicament and pressing an injection button while holding the injection device with the needle upwards. Another example of a priming operation performed with the injection device can include pressing a priming button of the injection device configured as an electric switch. Another example of a priming operation performed with the injection device can include attaching the energy source to a component of the injection device (e.g., plunger head) and/or attaching at least a component of the electronic system to a component of the injection device (e.g., plunger head or stopper) before pressing a priming button of the injection device. In some embodiments, the priming operation can include generating a trigger signal. The trigger signal can include at least one of a mechanical signal and an electrical signal.

In response to the priming operation (e.g., receiving the trigger signal), the energy source is coupled with the electronic component by a mechanism (e.g., gear mechanism) (304). In some embodiments, the mechanism can include one or more components (e.g., a plunger rod 108, a plunger head 109, as described with reference to FIGS. 1A-1F) configured to shift the energy source from one position, in which the energy source is electrically decoupled from the electronic component to a second position, in which the energy source is electrically coupled with the electronic component. Coupling the energy source with the electronic component can include shifting at least one pin of the energy source from one position to a second position such that both pins of the energy source contact the contact plates of the electronic component. In some embodiments, shifting the energy source from one position to a second position includes piercing an electrically insulating material (e.g., a portion of a stopper, as described with reference to FIGS. 1A and 1B, or an insulating membrane, as described with reference to FIGS. 1C and 1D). In some embodiments, the mechanism can include a switch configured to be activated for electrically coupling the energy source to the electronic component. Coupling the energy source with the electronic component, using a switch, can include bringing one or both pins of the energy source in electric contact with the contact plates of the electronic component.

In response to coupling the energy source with the electronic component, an electric signal is generated (306). The electric signal can be generated to assist and/or perform an operation of the injection device (e.g., control an administration of a medicament) and/or measure one or more parameters associated to the injection device (e.g., amount of a medicament, temperature, etc.). The electric signal can include generation of injection device data. The injection device data can include a unique identifier for the injection device, an amount of administered medicament, an amount of medicament within a cartridge and/or injection device, a medicament temperature, a timestamp of coupling the energy source to the electronic component, a location, and/or a situation specific data for the injection device.

The injection device data are transmitted to a processor to analyze one or more parameters associated with the administration of the medicament and the operational conditions of the injection device (308). For example, the injection device can be configured to transmit the data to an internal processor of the injection device to perform auto-correction of medicament administration or to an external processor that can coordinate storage of the data in a database, such as central database 212 described with reference to FIG. 2. In some embodiments, in response to successful transmission of data, the injection device can uncouple the energy source from the electronic component to conserve the energy of the energy source and process 300 can be repeated multiple times until the cartridge is emptied. In response to detecting that the cartridge is empty, the injection device can be separated in multiple segments to dispose of the energy source (e.g., battery) separately from the cartridge.

Figure 4:
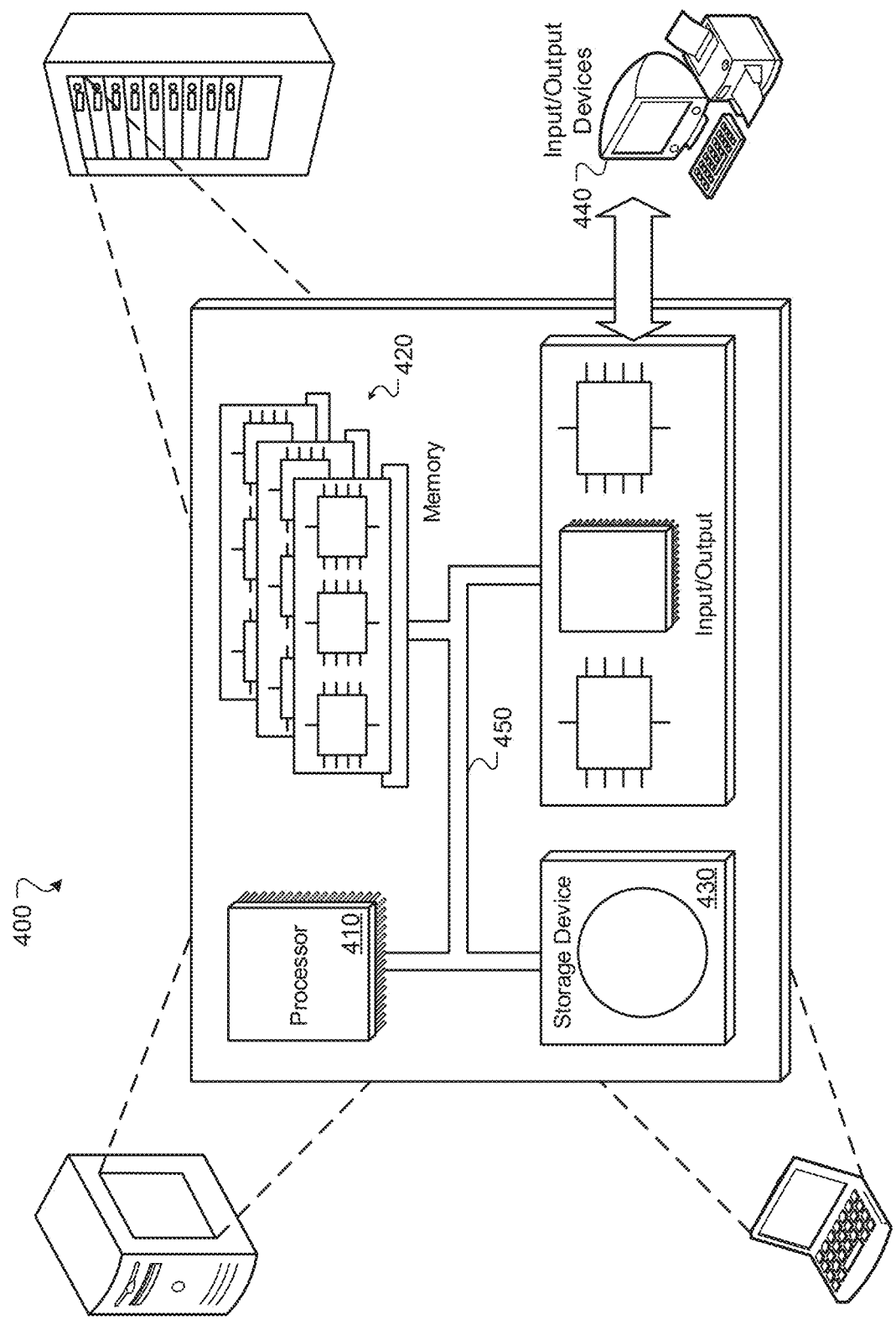
FIG. 4 is a schematic illustration of example computer systems.

FIG. 4 shows a schematic diagram of an example computing system 400. The system 400 can be used for the operations described in association with the embodiments described herein. For example, the system 400 may be included in any or all of the server components discussed herein. The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor.

In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit. The storage device 430 is capable of providing mass storage for the system 400. In one implementation, the storage device 430 is a computer-readable medium. In various different embodiments, the storage device 430 may be a floppy disk device, a hard disk device, an optical disk device, or a tape device. The input/output device 440 provides input/output operations for the system 400. In one implementation, the input/output device 440 includes a keyboard and/or pointing device. In another implementation, the input/output device 440 includes a display unit for displaying graphical user interfaces that enable a user to access data related to an item that is collected, stored and queried as described with reference to FIGS. 1-3.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described embodiments by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

A number of embodiments of the present disclosure have been described. Nevertheless, it will be understood that various modifications may be made without departing from the spirit and scope of the present disclosure. Accordingly, other embodiments are within the scope of the following claims.

REFERENCE NUMERALS

- 102 injection device
- 104 energy source
- 105 electronic component
- 106 medicament reservoir
- 107 plunger stopper
- 108 plunger rod
- 109 a plunger head
- 110 housing
- 111 bearing
- 112 dosage knob
- 113 needle
- 114 dosage window
- 115 needle assembly
- 116 needle cap
- 117 outer needle cap
- 118 cap
- 120 injection button
- 122 electrically insulating membrane
- 124 support
- 126a, 126b pins
- 126a cathode
- 126b anode
- 128a, 128b contact plates
- 130 external device
- 132 external processor
- 200 example system
- 202 network
- 204 injection device
- 206 central computer
- 210 central server
- 212 central database
- 214 entity
- 216 entity
- 218 entity
- 220 entity
- 222 healthcare continuum
- 224 energy source
- 226 electrical component
- 300 example process
- 400 computing system
- 410 processor
- 420 memory
- 430 storage device
- 440 input/output device
- 450 system bus

The invention claimed is:

1. An injection device comprising:
a stopper comprising at least one electronic component;
an energy source configured to move relative to the stopper; and
a plunger head of a plunger rod, the plunger head configured to engage the energy source to move the energy source from a first position, where the energy source is electrically decoupled from the at least one electronic component, to a second position, where the energy source is electrically coupled to the at least one electronic component.

2. The injection device of claim 1, wherein the energy source comprises a pin and the at least one electronic component comprises a contact plate.

3. The injection device of claim 2, wherein the stopper comprises an electrically insulating material and the pin is configured to pierce the electrically insulating material to electrically couple the energy source to the at least one electronic component.

4. The injection device of claim 2, wherein the plunger head is configured to move the energy source from the first position, where the pin of the energy source is electrically decoupled from the contact plate, to the second position, where the pin is electrically coupled to the contact plate.

5. The injection device of claim 1, wherein the energy source is positioned within a recess of the stopper in the first and second positions.

6. The injection device of claim 5, wherein the plunger head comprises a protrusion configured to enter the recess of the stopper.

7. The injection device of claim 1, wherein the at least one electronic component is at least one of a contact plate, an antenna, a sensor, a processor, and a motor.

8. The injection device of claim 1, wherein the energy source comprises a battery.

9. The injection device of claim 1, further comprising a medicament container comprising a medicament.

10. The injection device of claim 1, wherein the at least one electronic component comprises a processor configured to generate data related to the injection device when the energy source is electrically coupled to the at least one electronic component.

11. A method comprising:
electrically coupling an energy source of an injection device to at least one electronic component of the injection device by
moving a plunger rod of an injection device toward the energy source,
engaging a plunger head of the plunger rod to the energy source, and
moving the energy source toward the at least one electronic component.

12. The method of claim 11, wherein moving the energy source toward the at least one electronic component comprises piercing a stopper of the injection device.

13. The method of claim 12, wherein the stopper comprises the at least one electronic component.

14. The method of claim 11, wherein moving the energy source toward the at least one electronic component comprises moving the energy source from a first position, where a pin of the energy source is uncoupled from the at least one electronic component, to a second position, where the pin is electrically coupled to the at least one electronic component.

15. The method of claim 11, wherein moving the energy source toward the at least one electronic component comprises moving the energy source from a first position within a recess of a stopper of the injection device to a second position within the recess of the stopper.

16. The method of claim 11, further comprising selecting a dose of medicament by rotating a dosage knob of the injection device.

17. The method of claim 16, further comprising administering the selected dose of medicament of the injection device by moving an injection button of the injection device.

18. The method of claim 17, wherein administering the selected dose of medicament comprises displacing, by a stopper containing the at least one electronic component, the selected dose of medicament through a medicament container of the injection device.

19. The method of claim 17, wherein administering the selected dose of medicament comprises moving the energy source toward the at least one electronic component to cause the electrical coupling.

20. The method of claim 11, wherein engaging the plunger head of the plunger rod to the energy source comprises moving a protrusion of the plunger rod into a recess of a stopper of the injection device.

21. The method of claim 11, further comprising:
generating, by the at least one electronic component, data related to the injection device when the energy source is electrically coupled to the at least one electronic component; and
transmitting, by an antenna of the at least one electronic component, the generated data to an external device.

22. The method of claim 21, wherein the generated data comprises at least one of a unique identification number of the injection device, an amount of medicament delivered by the injection device, an amount of medicament within a cartridge of the injection device, a temperature of a medicament in the injection device, a timestamp of the electrical coupling of the energy source to the at least one electrical component, or a location of the injection device.

23. The method of claim 11, wherein electrically coupling the energy source to the at least one electronic component is performed during a priming of the injection device.

24. The method of claim 11, wherein electrically coupling the energy source to the at least one electronic component is performed prior to administering a medicament from the injection device.

25. The injection device of claim 1, wherein the plunger head is configured to move the energy source from the first position to the second position during a priming of the injection device.

26. The injection device of claim 1, wherein the plunger head is configured to move the energy source from the first position to the second position prior to administering a medicament from the injection device.

* * * * *